(12) United States Patent
Hartov et al.

(10) Patent No.: US 9,052,384 B2
(45) Date of Patent: Jun. 9, 2015

(54) SYSTEM AND METHOD FOR CALIBRATION FOR IMAGE-GUIDED SURGERY

(75) Inventors: Alexander Hartov, Enfield, NH (US); Keith D. Paulsen, Hanover, NH (US); David William Roberts, Lyme, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1027 days.

(21) Appl. No.: 12/994,044

(22) PCT Filed: May 22, 2009

(86) PCT No.: PCT/US2009/045082
§ 371 (c)(1),
(2), (4) Date: Jan. 21, 2011

(87) PCT Pub. No.: WO2009/143491
PCT Pub. Date: Nov. 26, 2009

(65) Prior Publication Data
US 2011/0153254 A1    Jun. 23, 2011

Related U.S. Application Data

(60) Provisional application No. 61/055,355, filed on May 22, 2008.

(51) Int. Cl.
*G10K 11/00* (2006.01)
*G01S 7/52* (2006.01)
*A61B 5/06* (2006.01)
*A61B 8/00* (2006.01)
*A61B 8/08* (2006.01)

(52) U.S. Cl.
CPC ............... *G01S 7/5205* (2013.01); *A61B 5/06* (2013.01); *A61B 8/4245* (2013.01); *A61B 8/483* (2013.01); *A61B 8/488* (2013.01); *A61B 8/5238* (2013.01); *A61B 8/0816* (2013.01)

(58) Field of Classification Search
USPC .......................................................... 702/103
See application file for complete search history.

(56) References Cited

U.S. PATENT DOCUMENTS

| 6,379,302 | B1 | 4/2002 | Kessman et al. |
| 6,961,405 | B2 * | 11/2005 | Scherch .......................... 378/65 |
| 7,085,400 | B1 | 8/2006 | Holsing et al. |
| 2004/0215072 | A1 * | 10/2004 | Zhu ................................ 600/407 |
| 2010/0208963 | A1 * | 8/2010 | Kruecker et al. ............. 382/131 |

FOREIGN PATENT DOCUMENTS

WO    2005099581 A1    10/2005

OTHER PUBLICATIONS

International Search Report and Written Opinion issued in related PCT Patent Application Serial No. PCT/US2009/045082, dated Jan. 7, 2010, 10 pages.

* cited by examiner

Primary Examiner — Tung S Lau
Assistant Examiner — Xiuquin Sun
(74) Attorney, Agent, or Firm — Lathrop & Gage LLP

(57) ABSTRACT

A method of calibrating a transformation of ultrasound data in an imaging system from a first coordinate system into a second coordinate system, the method including applying a transformation having parameters. The parameters are calibrated by imaging a planar object, extracting points corresponding to ultrasound rays intersecting the planar object, and fitting the parameters such that the points when transformed by the transformation describe a planar surface in the second coordinate system.

18 Claims, 3 Drawing Sheets

SYSTEM AND METHOD FOR CALIBRATION FOR IMAGE-GUIDED SURGERY

RELATED APPLICATIONS

The present application claims priority to U.S. provisional patent application No. 61/055,355, filed May 22, 2008, incorporated herein by reference.

US GOVERNMENT RIGHTS

Some of this material was developed with U.S. Government support through National Institutes of Health grant number R01 EB002082. The U.S. Government has certain rights in this invention.

FIELD

The present application relates to apparatus for combining imaging modalities, such as magnetic resonance imaging (MRI) or x-ray computed tomography (CT) with ultrasound imaging, to provide improved guidance during surgery.

BACKGROUND

Most tissues of the human body are soft tissues; these tissues are inherently flexible and readily deformable. Further, many of these soft tissues interface with other tissues along boundaries where considerable movement may take place. During surgery, as adjacent structures such as bone are moved and pressure applied with instruments such as retractors, these tissues will deform and shift. Since these tissues may deform readily both between imaging and surgery, and during surgery, it is common for surgeons to find tumors, foreign objects, organs, lesions, and other targets are no longer in the exact positions they occupied in preoperative images.

For a surgeon to properly treat or biopsy surgical targets, the surgeon must locate the correct targets during surgery. Further, for surgeons to avoid unintended damage to other structures, it may also be necessary to locate those other structures precisely during the surgery. While surgeons often locate targets visually, this is not practical when surgical targets are similar in appearance to nearby tissues, are located within organs, are in tight spots close to other organs, when damage to overlying or adjacent structures is to be minimized, or when exposure is otherwise difficult. It is desirable to locate these targets using medical imaging equipment during surgery.

MRI and CT imaging are often used with or without contrast enhancement to provide high resolution preoperative images of surgical targets. The equipment required to make these images is bulky, expensive, and not always easily incorporated into an operating-room environment. Further, the intense magnetic fields required for MRI may be incompatible with other operating room instruments and equipment, and radiation emitted by CT machines may require surgeon and staff leave the room during intraoperative imaging.

Ultrasound imaging equipment is generally less bulky and often far less expensive than MRI and CT equipment. Ultrasound equipment also does not emit electromagnetic radiation or magnetic fields, and is more compatible with the operating room environment. Unfortunately, it may not be possible for some targets to be properly identified in ultrasound images.

In Hartov, et al., Error Analysis for a Free-Hand Three Dimensional Ultrasound System for Neuronavgation, Neurosurgical Focus 6 (3), 5 Aug. 1999, it was suggested that targets found in preoperative MRI or CT images be located during neurosurgery by updating an image with ultrasound and a model of deformation of the brain. In that article, apparatus was proposed that used sensors produced by Ascension Technology Corporation, Milton, Vt., to track a handheld ultrasound transducer in three dimensions. Since not only the position, but the angle of the sensor, could be determined, an object in an image obtained with the transducer could be located to within a few millimeters in three dimensional space.

Other types of tracking devices have also been proposed for determining a location in three dimensions of the ultrasound transducer. For example, the transducer may be mounted to a linkage attached between the transducer and an object, the linkage attached with devices for monitoring motions of the transducer. It is also possible to use an optical tracking system for determining positions and angles of the transducer.

SUMMARY

A method of transforming ultrasound data in composite imaging system such as a system for obtaining ultrasound data and for aligning this data with previously obtained CT or MRI images. The ultrasound data is obtained in an ultrasound coordinate system. The method involves applying a transformation having parameters calibrated by steps including imaging a planar object, extracting points corresponding to ultrasound rays intersecting the planar object, fitting the parameters such that the points when transformed by the transformation describe a planar surface in the rectilinear coordinate system.

DETAILED DESCRIPTION OF THE EMBODIMENTS

System Overview

Figure 1:
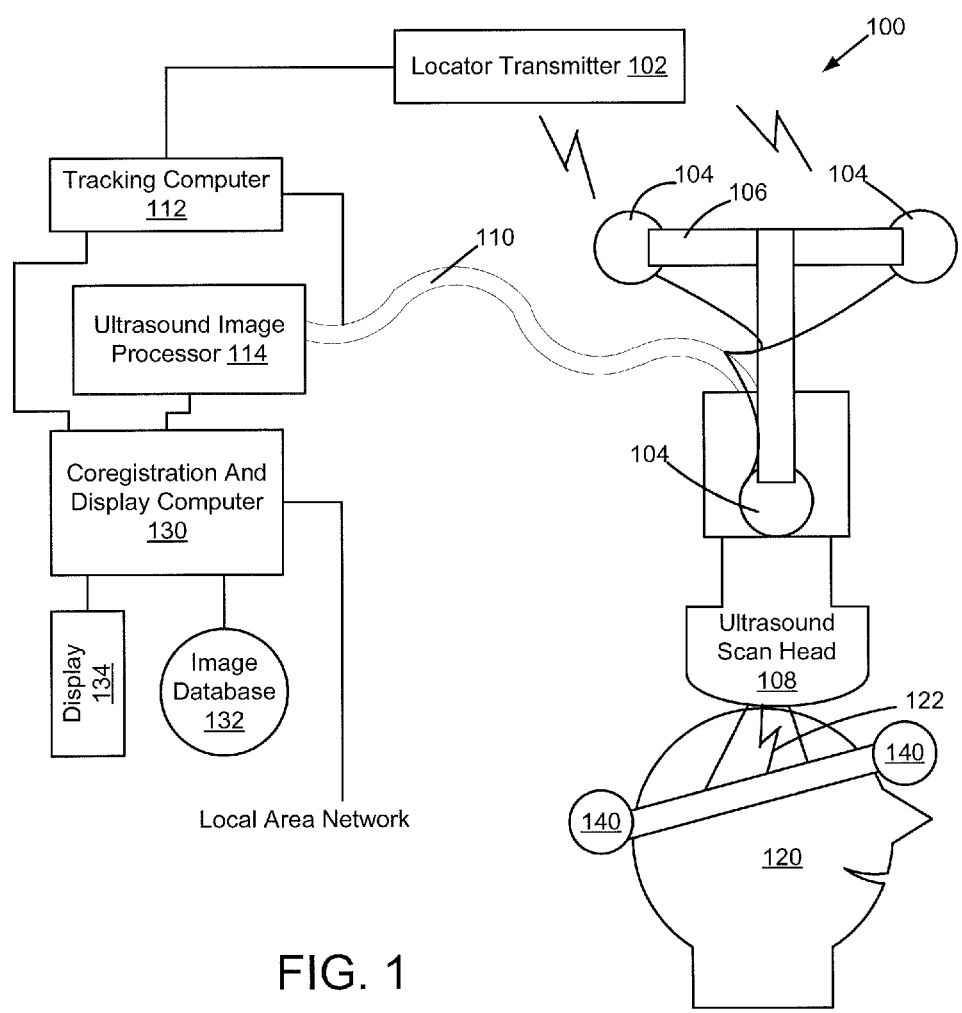
FIG. 1 is a block diagram of an imaging system for obtaining ultrasound images in an operating room and correlating those images to MRI or CT images.
Figure 2:
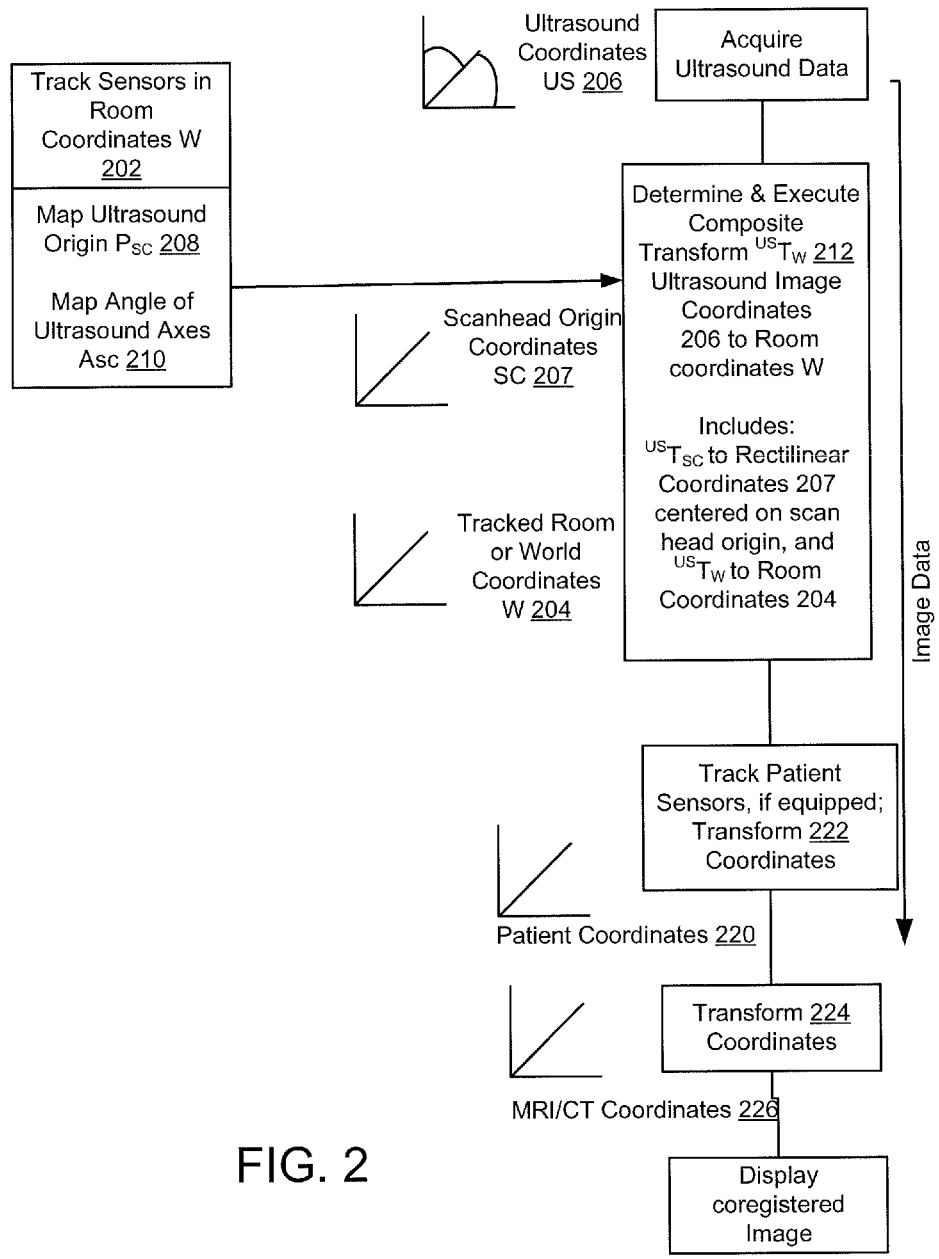
FIG. 2 illustrates the coordinate systems and coordinate transformations performed in the system of FIG. 1.
Figure 3:
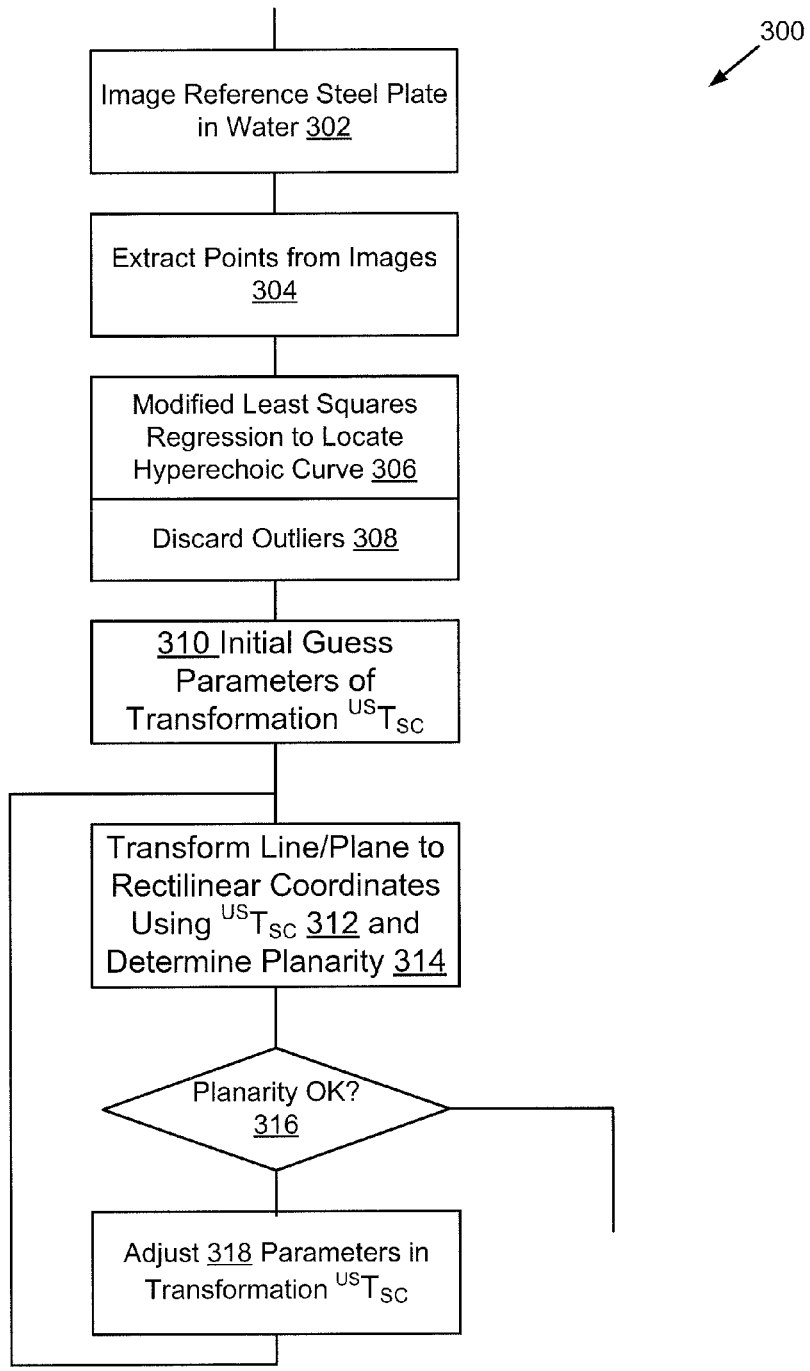
FIG. 3 is a flowchart of a method of calibration of a coordinate transformation.

An imaging system 100 is illustrated in FIG. 1. In this system, a locator transmitter 102, typically secured to an object in an operating room. The locator transmitter 102 may be secured to a wall, an operating table, or some other object that will not often move unexpectedly during an operation. In an embodiment having additional tracking sensors 140 (see below) attached to the patient, locator transmitter 102 may be attached to a movable object in the operating room.

The locator transmitter 102 transmits a signal to at least three locator sensors 104. Locator sensors 104 are attached to a rigid frame 106 that is also secured to an ultrasound medical imaging transducer head 108. A cable 110 connects transducer head 108 and locator sensors 104 to a tracking computer 112 and an ultrasound image processor 114. In an embodiment, transducer head 108 is adapted to be hand-held and freely moved.

Tracking computer 112 uses signals from the locator sensors 104 to track 202 the sensors 104 to determine a three-dimensional location of each locator sensor 104. The location sensors 104 are tracked in a three dimensional coordinate system relative to the locator transmitter 102 and herein referred to as room coordinates W 204. At least three sensors 104 are required, and these must not be located along a line.

Other embodiments may embody other apparatus for tracking location of the transducer head, such other apparatus may include mechanical linkages and optical tracking devices.

The ultrasound transducer head 108 may be placed in contact with a subject 120, whereupon it transmits ultrasound waves 122 into and receives echoes from the subject 120; imaging processor 114 thereupon constructs an ultrasound image from the echoes. In some embodiments, including those where the subject will move or be moved during surgery, additional tracking sensors 140 may optionally be attached to a halo attached to a subject.

In an embodiment, the ultrasound head 108 and imaging processor 114 constructs the ultrasound image according to a spherical set of ultrasound coordinates 206 having an axis and origin that are not fixed with relation to the room coordinates W 204. In alternative embodiment, the ultrasound head 108 and imaging processor 114 constructs the ultrasound image according to a Cartesian ultrasound coordinate system.

Coregistration and display computer 130 must dynamically determine a mapping between the room coordinates W 202 and the ultrasound coordinates 206. To do so, coregistration and display computer 130 inputs locations of all three sensors 104 in room coordinate W 204 terms from tracking computer 112. In embodiments having patient sensors 140, coregistration and display computer 130 inputs coordinates of those sensors also, these are used to dynamically determine a mapping between the room coordinates W 202 and presurgery imagery.

In determining these mappings, the system determines the locations of all three scanhead sensors 104. These locations are used to determine a location of the origin ($P_{SC}$) of the ultrasound coordinates 206. This location is mapped 208 relative to room coordinates ($F_W$). Also mapped are angles Asc 210 relative to room coordinates W of the center of the beam of ultrasound waves 122, and rotation of the head 108. From these angles Asc a calibrated transform function ($^{US}T_W$) is adjusted between the ultrasound spherical coordinate system 206 ($F_{US}$) first to an ultrasound rectilinear coordinate system ($F_{SC}$) 207 centered upon the scanhead origin ($P_{SC}$) and having axes aligned with the axes of the room rectilinear coordinate system W, and then to the room rectilinear coordinate system W 204. In some embodiments room coordinate system W 204 may be spherical.

Coregistration and display computer 130 also determines a transform 222 function between the room coordinates 204 ($F_W$) and a patient coordinate system 220 ($F_{PT}$). A transform 224 function between the patient coordinate system 222 and an magnetic resonance imaging or computed tomography coordinate system 226 ($F_{MR}$) used during prior imaging of the subject 120 is also determined; images from prior imaging of subject 120 are stored on an imaging database 132.

Once all these coordinate transform functions 212, 222, 224, are determined the ultrasound images in spherical or rectilinear coordinates from imaging processor 114 are continuously transformed according to a composite of the coordinate transform functions 212, 222, 224, and optionally a model of surgical deformation of tissues such as brain tissues, into coordinates associated with the prior imaging stored on imaging database 132. These transformed ultrasound images are thereby coregistered to the prior images from imaging database 132, they are then displayed on display 134, and updated as surgery proceeds and the scanhead 108 is moved.

Calibration to Determine the Transformation

An issue in performing the above-described processing is that of determining the transform functions 212, 222, and 224. In particular, the composite transformation $^{US}T_W$ 212 between the spherical or rectilinear ultrasound coordinate system 206 to the room coordinate system 204 is determined in part by a calibration procedure to determine the component transformation $^{US}T_{SC}$ that is performed in the operating room prior to surgery.

The transformation $^{US}T_W$ 212 has several key components. These include a transformation SCTW between rectilinear coordinates at the tracked scanhead origin Fsc and room coordinates W 204, and a transformation $^{US}T_{SC}$ that maps the ultrasound coordinates $F_{US}$ to the coordinates centered at the tracked scanhead origin $F_{SC}$ These transformations have inverses, $^{US}T_{SC}$ has inverse of $^{SC}T_{US}$; and $^{SC}T_W$ has inverse $^{W}T_{SC}$. If the coefficients of one of these transformations, such as $^{US}T_{SC}$, are known, the coefficients of its inverse transformation $^{SC}T_{US}$ are known, and vice versa.

Performing both transformations $^{US}T_{SC}$ (the inverse of $^{SC}T_{US}$) and $^{SC}T_W$ produces the composite transformation $^{US}T_W$.

Once an initial composite transformation $^{US}T_W$ 212 between the ultrasound coordinate system 206 and the room coordinate system 204 is determined, the scanhead origin location $F_{SC}$ (and transformation component $^{SC}T_W$) is continuously updated to allow for movement of the ultrasound scanhead 108. Also updated are the beam angle components of the transformation component $^{US}T_{SC}$ to allow for angular motions of the ultrasound scanhead 108.

Several methods have been proposed to determine the initial transformation $^{US}T_{SC}$, involving acquiring images of objects in known positions (i.e. known in terms of room coordinates W). These include methods using a single point defined by the intersection of wires, "N" arranged wires and objects with known shapes visible in ultrasound. These prior procedures required an operator to record the position of the tanks in which the various objects rested or of the objects themselves. An issue is that any error in recording the position or of positioning the objects results in an error in the calibration.

Calibration

In our calibration procedure 300, a calibration image is made of a reference plane, typically a steel plate or a tank bottom, in water 302. The method depends on producing sets of points from each image or volume which best describe the intersection of the image or volume with a plane of reference.

A formulation is proposed in which a plane whose position in absolute space is unknown is used. In this approach, the images of the plane in sequences of ultrasound images appear as easily identified strong echoes in the shape of a line intersecting the ultrasound images. The points on the images corresponding to the water/plane boundary are collected in a series of images. Based on an initial assumption about the calibration matrix $^{US}T_{SC}$, their position in rectilinear room coordinates W 204 or rectilinear coordinates Fsc 207 referenced to the scanhead origin is computed.

Since the water/plane boundary is known to be a plane, a measure of planarity is computed. Using this measure of planarity as an objective function, the matrix $^{US}T_{SC}$ is adjusted iteratively. This method works for both 2D ultrasound, where the plane-image intersection reduces to a line, and for 3D ultrasound where a portion of the plane is captured.

The method includes tracing rays emanating from the scan head 108. Image intensity along those rays is filtered using an eleven-points centered average $$\left(I_{filtered,i} = \frac{1}{11} \sum_{j=i-5}^{i+5} I_j\right)$$

so as not to introduce a spatial phase shift to the filtered data, in order to reduce the effect of ultrasound artifacts. Intensity is then normalized and used to find the point at which the relative filtered intensity jumps above a threshold value, as the ray moves away from the scan head 108. The value of the threshold was determined experimentally to result in a curve which would follow the transition (maximum gradient) between water (dark pixels) and steel (very bright pixels). In an embodiment, it was found that by setting that threshold to 0.5 we had best results. These points are collected and plotted in the image or volume. The first few pixels or voxels in a ray are set are set to zero to eliminate high intensity values seen at the edge of the transducer.

The identification of the threshold defined by the reflections on the steel plate is aided by adjusting ultrasound system parameters as the reference plate is imaged during calibration. For example, reducing the transmitted ultrasound beam intensity helps the process by making the plane of interest appear as a bright single line in the images. Reduced beam intensity also reduces imaging artifacts caused by echoes from the sides of the tank, the water surface, or the scan head 108 itself.

Points are extracted 304 from the images. For most reliable results when using a spherical or polar coordinate system, we use rays emanating from the transducer, whether it is a curved linear of a 3D one. Each line is traced starting at the top and towards the bottom, corresponding approximately to moving away from the scan head 108 along rays emanating from the transducer center. When using rectilinear ultrasound coordinates, lines are traced in columns.

As a way to speed up calculations in either spherical or rectilinear ultrasound coordinates we take only every $5^{th}$ column of image data. This shortcut did not seem to be detrimental to the robustness of the algorithm.

With 2D images, the points collected in this fashion form a cluster along the hyperechoic plane intersection. They will not necessarily be collinear, and there may be a significant number of far outliers which may foul traditional methods of computing the least square regression line.

A least-squares regression 306 to represent the hyperechoic plane as a line is performed with an adaptive method to compute the line of intersection. This method gradually eliminates 308 the farthest outliers until all the points that remain are within some predetermined distance of the resulting least squares curve. Points not discarded are retained for use in the calibration algorithm. In an embodiment, this is performed using a modified RANSAC algorithm. RANSAC algorithms (RANdom SAmple Consensus) were described by Fischler & Bolles in 1981 algorithm.

Two sets of points are collected for each image, which represent the end points of the line of intersection between the reference plane and the ultrasound as it appears in each image.

The parameters defining the plane of reference, expressed in the 3D volume's coordinate system (Fus) are used to compute the intersection points between this idealized plane and the four rays defining the edges of the frustum. Thus four points are obtained from each 3D data set to be used in the optimization procedure that follows.

When transforming the points obtained from the images or volumes we use the previously described transformations, $^{US}T_{SC}$ which relates ultrasound coordinates to the scanhead origin and $^{SC}T_W$ which relates tracked coordinates of the scanhead origin to world coordinates. The parameters defining the transformation matrix $^{US}T_{SC}$ are initially unknown. If all the transformations leading from ultrasound space to room space are correct, then the points identified in the images or volumes as representing the plane intersections of rays or columns with the reference plate will describe a plane when expressed in the rectilinear coordinates.

The computation is formulated as a minimization problem in which the "planarity" of the points transformed to world coordinates needs to be optimized. In one algorithm, we
1) Initialize transformation matrix $^{US}T_{SC}$ to an initial guess 310 which in a particular embodiment is a result of a previous calibration.
2) Transform 312 the points extracted from the images to rectilinear room coordinates W 204 using transformation $^{US}T_W$, which includes transformations $^{US}T_{SC}$ and $^{SC}T_W$.
3) Perform a plane fit, preferably using the singular value decomposition on the points' coordinates 314.
4) If 316 the transformed data is sufficiently planar or if a maximum number of iterations have been reached, the calibration ceases.
5) If the data is not sufficiently planar, the parameters of the transformation $^{US}T_{SC}$ are adjusted 318.
6) Repeat steps 2-5

During the updating of $^{US}T_{SC}$ we have 6 parameters to adjust (tx, ty, tz) and (θx, θy, θz) in order to maximize the planarity of the points obtained from ultrasound data and transformed to world coordinates. We have experimented with two algorithms to solve this problem, the first using a gradient descent (GD) and one being an adaptation of the simulated annealing algorithm (SA).

In both methods, the planarity of point sets is calculated using the singular values decomposition method (SVD). The SVD produces the optimum plane parameters to the problem of minimizing the cumulative shortest (e.g. perpendicular to the plane) distance between a plane and a given set of points. The cumulative distance (RMS) is given as a byproduct of the plane parameters computation.

Our implementation of the gradient descent search is based on the numerical computation of the gradient of the objective function and the use of an adjustable step size. The size of the update step in the direction of the gradient is increased (d←d* (1+α)) upon reductions in the objective function, and decreased otherwise (d←d*(1+α)), with α=5%.

We also used a modified simulated annealing algorithm to solve the optimization parameters; the six variables are updated at every iteration by adding a random value that is uniformly distributed in the range +/−1 and scaled by a step size. Step sizes are different for angular and translation variables because of the different sensitivities to these variables of the objective function. The step size is increased by a large factor within limits every time an improvement is obtained in the objective function, thus increasing the search space around the current optimum point. Conversely, any time an improvement is not obtained, the step size is reduced by a small factor. Thus the search space is gradually reduced to the neighborhood around the current optimum. Furthermore, the ratio of the adjustment factors regulates how long the program searches the farther reaches of the search space, compared to the close neighborhood of the current optimum point.

In an embodiment, the search space is constrained to reasonable ranges based upon scanhead angles and positions that are expected to be possible given known mechanical constraints of the system and physical coupling that may exist between the ultrasound scanhead and the tracker.

The method we developed for 2D images extends naturally to 3D volumes. In a particular embodiment in which the ultrasound coordinates were a spherical coordinate system, 3D data is organized in a 3D array indexed by $(r, \theta, \phi)$, where $r$ is the distance from the transducer origin, with $\theta$ and $\phi$ are angles along perpendicular directions. This is a spherical coordinate system that encompasses a volume in the shape of a frustum. Step sizes in the radial and both angular coordinates are given so that a voxel's location in space is easily computed. The effective tangential resolution of this system decreases as one moves away from the transducer. This indexing method is advantageous for our technique in identifying the intersection of the plane with the frustum of ultrasound data in that we can easily search along rays, since they represent the principal indexing direction. From the points obtained by thresholding we compute a plane that best fits these points. The computation of the plane that best fits the point set is based on minimizing the cumulative shortest absolute distances of the individual points from the plane and is based on a singular values decomposition of the least squares problem. We use an adaptive approach by discarding outliers until the remaining points are within a narrow slice of space on both sides of the plane that fits them best.

In an alternative embodiment, a rectilinear coordinate system for 3D data may be used in place of the spherical coordinate system described in the above paragraph.

While the forgoing has been particularly shown and described with reference to particular embodiments thereof, it will be understood by those skilled in the art that various other changes in the form and details may be made without departing from the spirit hereof. It is to be understood that various changes may be made in adapting the description to different embodiments without departing from the broader concepts disclosed herein and comprehended by the claims that follow.

What is claimed is:

1. A method of calibrating a transformation of 3-dimensional ultrasound data in an imaging system from a first coordinate system into a second coordinate system, the method calibrating a-transformation having parameters and calibrating the transformation by steps comprising:
    imaging, with a 3-dimensional ultrasound imaging system, an object having a planar surface to provide a first ultrasound data in the first coordinate system;
    extracting points corresponding to ultrasound rays intersecting the planar surface of the object from the first ultrasound data; and
    fitting the parameters such that the points when transformed by the transformation describe a planar surface in the second coordinate system;
    and using the calibrated transformation by:
    obtaining additional ultrasound images using the 3-dimensional ultrasound imaging system, the additional ultrasound images being images of a patient undergoing surgery obtained in a spherical coordinate system; and
    using the transformation with the fitted parameters to coregister the additional ultrasound images to images in a rectilinear coordinate system.

2. The method of claim 1 wherein the points are filtered to remove outliers.

3. The method of claim 2 wherein the imaging system comprises at least one ultrasound imaging head attached to at least one tracking device, the tracking device configured to determine coordinates of the ultrasound imaging head, and wherein the first coordinate system is an ultrasound coordinate system.

4. The method of claim 3 wherein the tracking device is configured to determine an angle of the ultrasound imaging head.

5. The method of claim 4 further comprising automatically updating the transformation on a coregistration and display computer for at least one of changes in the angle of the ultrasound imaging head, and changes in position of the ultrasound imaging head.

6. The method of claim 5 wherein the transformation from the first coordinate system into the second coordinate system is a composite of transformation from the first coordinate system into a room coordinate system, and a transformation from the room coordinate system into a patient coordinate system.

7. The method of claim 3 wherein the tracking device comprises at least three non-collinear sensors attached to ultrasound imaging head.

8. The method of claim 1 wherein the first coordinate system is selected from the group consisting of a rectilinear coordinate system and a spherical coordinate system.

9. The method of claim 1 wherein the parameters are fitted by simulated annealing.

10. The method of claim 1 wherein the parameters are fitted by gradient descent.

11. The method of claim 1 wherein the parameters are fitted by at least one method selected from gradient descent and simulated annealing,
    wherein the fitting comprises transforming the extracted points into the second coordinate system, and determining planarity of the points in the second coordinate system;
    wherein the imaging system comprises at least one ultrasound imaging head attached to at least one tracking device, the at least one tracking device configured to determine coordinates of the ultrasound imaging head and to determine an angle of the ultrasound imaging head; and
    wherein the first coordinate system is an ultrasound coordinate system.

12. The method of claim 11 wherein the transformation from the first coordinate system into the second coordinate system is a composite of transformation from the first coordinate system into a room coordinate system, and a transformation from the room coordinate system into a patient coordinate system.

13. The method of claim 1 wherein the first coordinate system is a spherical coordinate system, and the second coordinate system is a rectilinear coordinate system.

14. The method of claim 1 wherein the parameters are fitted by simulated annealing.

15. The method of claim 1 wherein the parameters are fitted by gradient descent.

16. The method of claim 1 wherein the imaging system comprises at least one ultrasound imaging head attached to at least one tracking device, the tracking device configured to determine coordinates and an angle of the ultrasound imaging head, and where the transformation is automatically updated for changes in position and angle of the ultrasound imaging head.

17. The method of claim 1 wherein the transformation from the first coordinate system into the second coordinate system is a composite of transformation from the first coordinate system into a room coordinate system, and a transformation from the room coordinate system into a patient coordinate system.

18. A method of calibrating a transformation of ultrasound data in an imaging system from a first coordinate system into a second coordinate system, the method of calibrating comprising applying in a processor the transformation having parameters and calibrating the transformation by steps comprising:

imaging an object having a planar surface with an ultrasound imaging system;

extracting points corresponding to ultrasound rays intersecting the planar surface of the object; and fitting the parameters such that the points when transformed by the transformation describe a planar surface in the second coordinate system;

wherein fitting the parameters involves finding cumulative shortest absolute distances of the individual points from the planar surface in the second coordinate system;

and using the calibrated transformation by:

obtaining additional ultrasound images using the 3-dimensional ultrasound imaging system, the additional ultrasound images being images of a patient undergoing surgery obtained in a spherical coordinate system; and using the transformation with the fitted parameters to coregister the additional ultrasound images to images in a rectilinear coordinate system.

\* \* \* \* \*